(12) United States Patent
Finley (10) Patent No.: US 12,232,749 B2
(45) Date of Patent: Feb. 25, 2025

(54) DRILL GUIDE FOR ORTHOPEDIC DEVICE

(71) Applicant: Zimmer, Inc., Warsaw, IN (US)

(72) Inventor: Adam Finley, Winona Lake, IN (US)

(73) Assignee: Zimmer, Inc., Warsaw, IN (US)

(*) Notice: Subject to any disclaimer, the term of this patent is extended or adjusted under 35 U.S.C. 154(b) by 6 days.

(21) Appl. No.: 17/991,484

(22) Filed: Nov. 21, 2022

(65) Prior Publication Data
US 2023/0088523 A1 Mar. 23, 2023

Related U.S. Application Data

(63) Continuation of application No. 16/961,832, filed as application No. PCT/US2019/019843 on Feb. 27, 2019, now Pat. No. 11,529,150.

(60) Provisional application No. 62/636,073, filed on Feb. 27, 2018.

(51) Int. Cl.
*A61B 17/80* (2006.01)
*A61B 17/17* (2006.01)

(52) U.S. Cl.
CPC ........ *A61B 17/1728* (2013.01); *A61B 17/809* (2013.01)

(58) Field of Classification Search
CPC .............. A61B 17/0684; A61B 17/809; A61B 17/7233
See application file for complete search history.

(56) References Cited

U.S. PATENT DOCUMENTS

| | | | | |
|---|---|---|---|---|
| 3,716,050 A | * | 2/1973 | Johnston | A61B 17/8061 606/286 |
| 4,565,193 A | * | 1/1986 | Streli | A61B 17/809 606/67 |
| 5,015,248 A | * | 5/1991 | Burstein | A61B 17/68 606/328 |
| 5,586,985 A | * | 12/1996 | Putnam | A61B 17/809 606/904 |
| 5,601,553 A | | 2/1997 | Trebing et al. | |

(Continued)

FOREIGN PATENT DOCUMENTS

| | | |
|---|---|---|
| AU | 2019227788 A1 | 7/2020 |
| AU | 2019227788 B2 | 5/2024 |

(Continued)

OTHER PUBLICATIONS

"U.S. Appl. No. 16/961,832, Corrected Notice of Allowability mailed May 17, 2022", 3 pgs.

(Continued)

*Primary Examiner* — Anu Ramana
(74) *Attorney, Agent, or Firm* — SCHWEGMAN LUNDBERG & WOESSNER, P.A.

(57) ABSTRACT

A bone plate system for use with fasteners for fixation of a fractured bone, including a bone plate having an elongate shaft for placement against the bone. The bone plate further has at least one threaded hole for receiving at least one fastener, with each hole having a central axis. The plate further has a bone contacting first surface, an opposite second surface, a thickness extending in a dimension between said first and second surfaces; and at least one tubular drill guide cap. The drill guide cap is engageable with a first hole of at least one threaded hole, the cap having a threaded exterior, an internal bore, a proximal end, and a distal end.

9 Claims, 5 Drawing Sheets

(56) References Cited

U.S. PATENT DOCUMENTS

| | | | |
|---|---|---|---|
| 5,662,655 A * | 9/1997 | Laboureau | A61B 17/0642 606/301 |
| 7,207,993 B1 * | 4/2007 | Baldwin | A61B 17/74 606/65 |
| 7,229,445 B2 * | 6/2007 | Hayeck | A61B 17/74 606/70 |
| 8,062,294 B2 * | 11/2011 | Reynolds | A61B 17/8052 606/301 |
| 9,113,970 B2 | 8/2015 | Lewis et al. | |
| 9,675,395 B2 * | 6/2017 | Averous | A61B 17/0644 |
| 9,730,742 B2 | 8/2017 | Lewis et al. | |
| 9,788,872 B2 * | 10/2017 | Wagner | A61B 17/80 |
| 9,833,270 B2 * | 12/2017 | Zlotolow | A61B 17/80 |
| 9,839,458 B2 * | 12/2017 | Bouduban | A61F 2/0811 |
| 10,004,603 B2 * | 6/2018 | Appenzeller | A61B 17/8085 |
| 10,117,689 B2 | 11/2018 | Zlotolow | |
| 10,130,403 B2 | 11/2018 | Lewis et al. | |
| 11,529,150 B2 | 12/2022 | Finley | |
| 2006/0015123 A1 | 1/2006 | Fencl et al. | |
| 2007/0233111 A1 | 10/2007 | Orbay et al. | |
| 2008/0015591 A1 | 1/2008 | Castaneda et al. | |
| 2008/0015694 A1 * | 1/2008 | Tribus | A61B 17/7059 623/17.11 |
| 2009/0118770 A1 | 5/2009 | Sixto, Jr. et al. | |
| 2009/0275987 A1 * | 11/2009 | Graham | A61B 17/8061 606/280 |
| 2011/0015682 A1 | 1/2011 | Lewis et al. | |
| 2011/0224737 A1 | 9/2011 | Lewis et al. | |
| 2012/0089192 A1 | 4/2012 | Biedermann | |
| 2021/0077127 A1 | 3/2021 | Finley | |

FOREIGN PATENT DOCUMENTS

| | | |
|---|---|---|
| DE | 112019001027 T5 | 11/2020 |
| GB | 2585283 A | 1/2021 |
| GB | 2585283 B | 2/2022 |
| JP | 2013006037 | 1/2013 |
| JP | 2013542770 | 11/2013 |
| JP | 2014046200 | 3/2014 |
| JP | 2021513909 A | 6/2021 |
| JP | 7534225 | 8/2024 |
| WO | WO-2019168988 A1 | 9/2019 |

OTHER PUBLICATIONS

"U.S. Appl. No. 16/961,832, Final Office Action mailed Oct. 5, 2021", 9 pgs.

"U.S. Appl. No. 16/961,832, Non Final Office Action mailed Jan. 28, 2022", 8 pgs.

"U.S. Appl. No. 16/961,832, Non Final Office Action mailed Jun. 15, 2021", 7 pgs.

"U.S. Appl. No. 16/961,832, Notice of Allowance mailed May 3, 2022", 6 pgs.

"U.S. Appl. No. 16/961,832, Notice of Allowance mailed Aug. 18, 2022", 6 pgs.

"U.S. Appl. No. 16/961,832, Preliminary Amendment filed Jul. 13, 2020", 3 pgs.

"U.S. Appl. No. 16/961,832, Response filed Jan. 5, 2022 to Final Office Action mailed Oct. 5, 2021", 10 pgs.

"U.S. Appl. No. 16/961,832, Response filed Apr. 21, 2022 to Non Final Office Action mailed Jan. 28, 2022", 8 pgs.

"U.S. Appl. No. 16/961,832, Response filed Sep. 14, 2021 to Non Final Office Action mailed Jun. 15, 2021", 8 pgs.

"International Application Serial No. PCT/US2019/019843, International Preliminary Report on Patentability mailed Sep. 3, 2020", 6 pgs.

"International Application Serial No. PCT/US2019/019843, International Search Report mailed May 31, 2019", 2 pgs.

"International Application Serial No. PCT/US2019/019843, Written Opinion mailed May 31, 2019", 4 pgs.

"United Kingdom Application Serial No. 2012653.8, Examination Report under Section 18(3) mailed Aug. 31, 2021", 4 pgs.

"United Kingdom Application Serial No. 2012653.8, Intention to Grant under Section 18(4) mailed Nov. 16, 2021", 2 pgs.

"United Kingdom Application Serial No. 2012653.8, Response filed Oct. 1, 2021 to Examination Report under Section 18(3) mailed Aug. 31, 2021", 8 pgs.

U.S. Appl. No. 16/961,832, filed Jul. 13, 2020, Drill Guide for Orthopedic Device.

"Japanese Application Serial No. 2020-567469, Final Notification of Reasons for Refusal mailed Jan. 23, 2024", w/ English Translation, 4 pgs.

"Japanese Application Serial No. 2020-567469, Response filed Nov. 2, 2023 Final Notification of Reasons for Refusal mailed Aug. 8, 2023", W/ English Claims, 6 pgs.

"Japanese Application Serial No. 2020-567469, Response filed Apr. 1, 2024 to Final Notification of Reasons for Refusal mailed Jan. 23, 2024", W/ English Claims, 6 pgs.

"Japanese Application Serial No. 2020-567469, Office Action mailed Jan. 31, 2023", w English Translation, 10 pgs.

"Japanese Application Serial No. 2020-567469, Response filed May 1, 2023 to Office Action mailed Jan. 31, 2023", w English claims, 9 pgs.

"Japanese Application Serial No. 2020-567469, Final Notification of Reasons for Refusal mailed Aug. 8, 2023", w English Translation, 7 pgs.

"Australian Application Serial No. 2019227788, First Examination Report mailed Nov. 9, 2023", 5 pgs.

"Australian Application Serial No. 2019227788, Response filed Jan. 31, 2024 to First Examination Report mailed Nov. 9, 2023", 17 pgs.

* cited by examiner

DRILL GUIDE FOR ORTHOPEDIC DEVICE

CROSS REFERENCE

This Application is a continuation of U.S. patent application Ser. No. 16/961,832 filed Jul. 13, 2020, now issued as U.S. Pat. No. 11,529,150, which is a U.S. national phase entry under Section 371 of International Application No. PCT/US2019/019843 filed Feb. 27, 2019 and published in English as WO 2019/168988 A1, which claims the benefit of priority under 35 U.S.C. § 119 (e) to U.S. Provisional Patent Application Ser. No. 62/636,073 filed Feb. 27, 2018. The contents of each of the prior applications are incorporated by reference herein.

BACKGROUND OF THE INVENTION

Technical Field

This invention relates broadly to surgical devices. More particularly, this invention relates to orthopedic implants, and specifically to bone plates and drill guides.

Background Information

Improper treatment of a fracture to the metaphysis of a long bone can result in deformity and long-term discomfort. Alignment and fixation of a metaphyseal fracture are typically performed by one of several methods: casting, external fixation, pinning, and plating.

Casting is non-invasive, but it may not be able to maintain alignment of the fracture where many bone fragments exist. Therefore, as an alternative, external fixators may be used.

External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments.

Pinning with K-wires (Kirschner wires) is an invasive procedure whereby pins are positioned into the various fragments. This is a difficult and time-consuming procedure that provides limited fixation if the bone is comminuted or osteoporotic.

Plating utilizes a stabilizing metal plate typically placed against the bone, fixed-angle pegs (which may have threaded or non-threaded shafts) positioned through the plate and entering drilled holes adjacent an articular bone surface, and cortical screws extending from the plate into holes drilled in the bone to provide stabilized fracture fixation.

When fixed-angle pegs are utilized in conjunction with a bone plate, it is necessary to ensure that the pilot holes drilled for the pegs are co-axial with the hole axes. Otherwise, the shaft of the pegs will not properly align with the anatomy, and the head of the pegs will not properly align with the threaded holes of the plate, potentially resulting in cross-threading. As a result, with the plate placed upon the bone, prior to drilling each hole in the bone in alignment with a peg hole, a drill guide is attached to the plate at the peg hole. The guide defines a tubular passage which directs the drill bit in the proper orientation for a peg through the particular peg hole. After drilling each hole, the drill guide is removed, the peg is inserted in the peg hole, and the drill guide is coupled to a subsequent peg hole.

The process of attaching the drill guide during the surgical procedure is laborious. It can be difficult to locate the appropriate angle for threadably coupling the guide to the peg hole during the procedure, given that each peg hole may have a discrete axis angle from the other peg holes. Such difficulty can unnecessarily prolong the surgical procedure. Additionally, in many systems, even systems in which the drill guide is built into the peg, the profile of the system is too tall for use in all situations.

What is needed in the art is plugs that are preassembled and supplied sterile on the plate so that the drill guide is built into the removal tool instead of the plug and wherein the plug is adaptable to a variety of plate thicknesses so that the same plug/peg/insert can be used for all plates in a system instead of having to fit specific inserts to a specific plate thickness.

SUMMARY OF THE INVENTION

A bone plate system for use with fasteners for fixation of a fractured bone, includes a bone plate having an elongate shaft for placement against the bone. The bone plate further has at least one threaded hole for receiving at least one fastener, with each hole having a central axis. The plate further has a bone contacting first surface, an opposite second surface, a thickness extending in a dimension between the first and second surfaces; and at least one tubular drill guide cap. The drill guide cap is engageable with a first hole of at least one threaded hole, the cap having a threaded exterior, an internal bore, a proximal end, and a distal end.

A bone plate system for use with fasteners for fixation of a fractured bone, includes a bone plate having an elongate shaft for placement against a bone The bone plate further has at least one threaded hole for receiving at least one fastener, with each hole having a central axis. The plate further has a bone contacting first surface, an opposite second surface, a thickness extending in a dimension between the first and second surfaces, and at least one tubular drill guide cap. The drill guide cap is engageable with a first hole of at least one threaded hole, the cap having a threaded exterior, an internal bore, a proximal end, and a distal end. A cap removal tool, having a proximal end, a tool longitudinal axis and a distal end, the tool longitudinal axis and the central axis being coaxial, with the distal end shaped to engage the proximal end of the cap, with the cap and the tool being releasably connectable.

A method for fixing a fractured bone includes providing alignment caps prepackaged on a bone plate. An extraction tool, having a tool longitudinal axis and an extraction tool bore in the direction of the tool longitudinal axis, is placed into the drill guide cap, the cap having a central axis, to align the central axis with the extraction tool longitudinal axis. The extraction tool is used to guide a drill, the drill having a drill bit inserted into the extraction tool bore. Preparing the bone using the drill. Removing the drill. Using the extraction tool to remove the alignment drill guide.

These, and other objects, features and advantages of this invention will become apparent from the following detailed description of the various aspects of the invention taken in conjunction with the accompanying drawings.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

Corresponding reference characters indicate corresponding parts throughout the several views. The exemplary embodiments set forth herein are not to be construed as limiting the scope of the invention in any manner.

DETAILED DESCRIPTION OF THE INVENTION

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
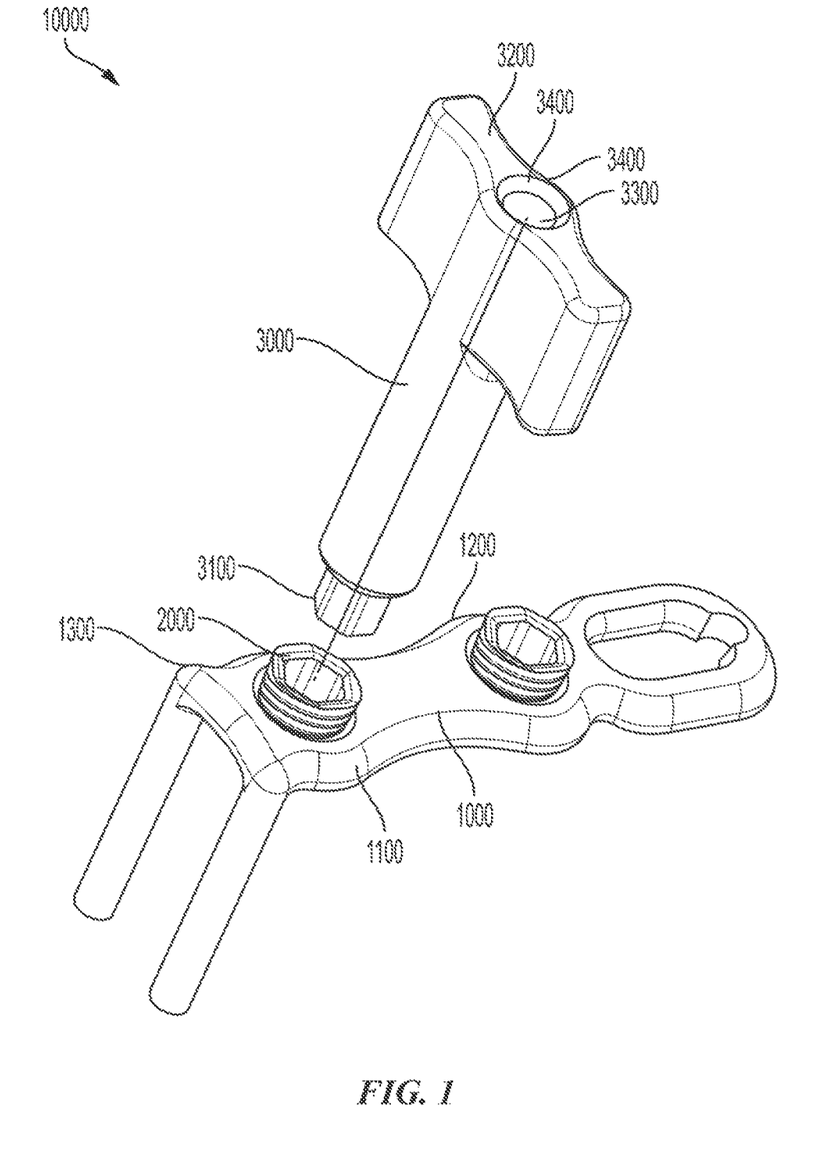
FIG. 1 shows a perspective view of a bone plate system in accordance with the present invention.
Figure 2:
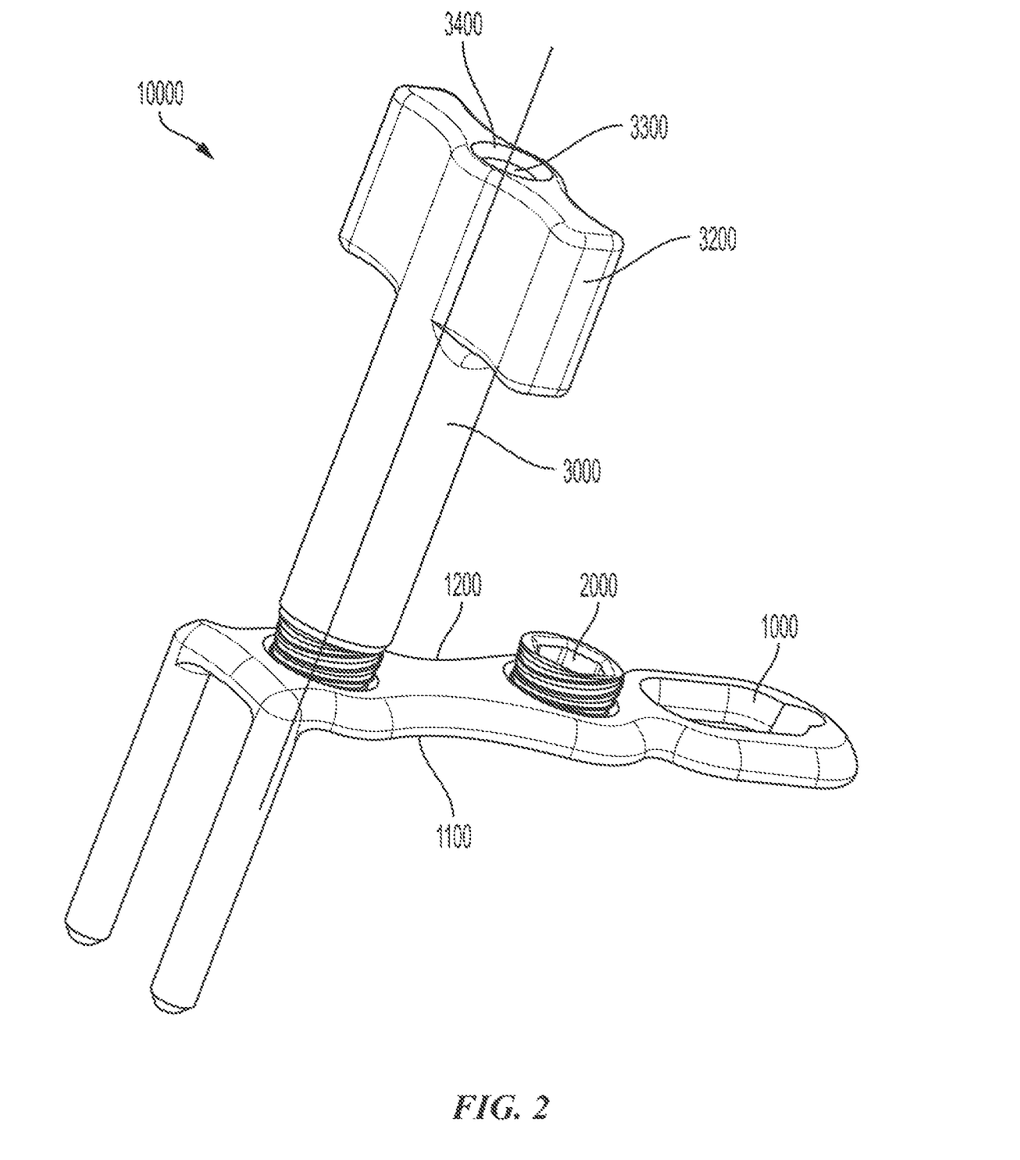
FIG. 2 shows a perspective view of the bone plate system of FIG. 1 with a guide tool engaged with a guide cap inserted in a bone plate.
Figure 3:
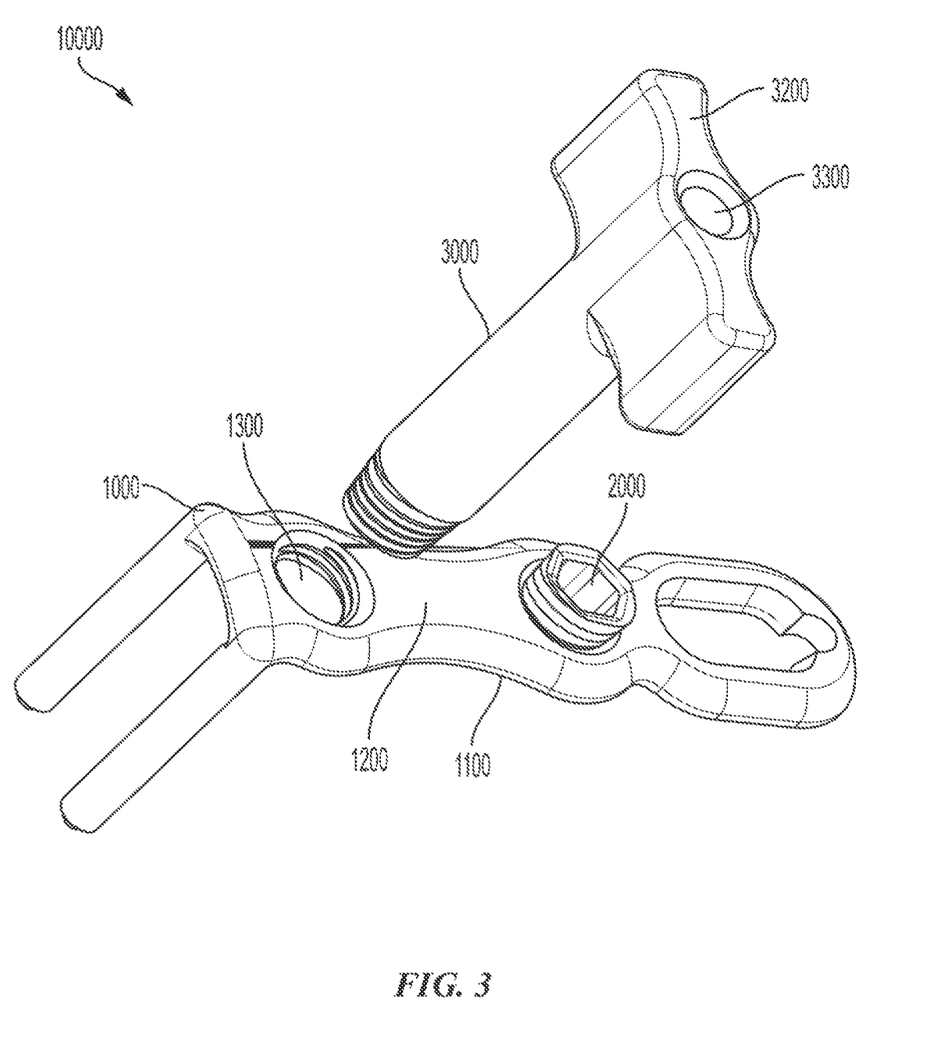
FIG. 3 shows a perspective view of the bone plate system of FIG. 1 with a guide tool engaged with the guide cap that has been removed from a bone plate.

Referring now generally to FIGS. 1-3, there is shown bone plate system 10000. Plate system 10000 generally includes a bone plate 1000, a plurality of guide caps 2000, and an insertion and extraction tool 3000. Insertion and extraction tool 3000 may be referred to as an insertion tool or an extraction tool but tool 3000 may perform both insertion and extraction functions. Insertion and extraction tool 3000 further has a tool longitudinal axis 3400 and an extraction tool bore 3300 extending axially. Bone plate 1000 is adapted for placement over the shaft of a bone (not shown). The term guide cap 2000 may also be referred to by terms "guide tip" or "guide pin" or guide plug.

Referring still to FIGS. 1-3, bone plate 1000 includes a generally flat shape, a bone contacting surface 1100 and a top surface 1200. Bone plate 1000 further includes a plurality of threaded holes 1300 for threadably receiving drill guide caps 2000. The holes are shown as cylindrical, but may be of any shape.

Referring now to FIGS. 1-3 and 5, each drill guide cap 2000 is shown with a generally cylindrical exterior shape. The drill guide cap need not be cylindrical and may be a tubular structure of any suitable perimeter shape. Each drill guide cap 2000 further includes an internal surface and an internal bore 2100 having a longitudinal axis 2200, a proximal end 2300, and a distal end 2400. Each drill guide cap 2000 preferably further includes a removal tool receiving opening at proximal end 2300. The removal tool receiving opening may be, for example, circular. Guide caps 2000 are used as a sole guide for a drill bit (not shown) for use with seating bone plate 1000 on a bone.

Referring again to FIGS. 1-3, insertion and extraction tool 3000 for drill guide caps 2000, includes a distal working end 3100 and a proximal drive handle end 3200. Guide caps 2000 may be inserted or extracted by insertion and extraction tool 3000. Distal working end 3100 preferably has a tapered square for engaging a circular opening at the proximal end 2300 of each drill guide cap 2000. The edges of the square driver are sized to provide sufficient frictional force to rotate the cap 2000 into and out of engagement with plate 1000. Other suitable engagements may be used as well. For example, guide caps 2000 may have a proximal end 2300 with a hex shape, or any non-circular exterior cross-sectional shape, that will facilitate torque transmission. When drill guide caps 2000 are connected to plate 1000 at a threaded hole 1300, using insertion and extraction tool 3000, the longitudinal axis 2200 of each guide cap 2000 may be coaxial with the axis of the respective threaded hole 1300 of plate 1000 in which the cap 2000 is inserted. Furthermore, extraction tool 3000 may be inserted into guide cap 2000 to a depth that may be at least the height of the guide cap cylinder 2000. When drill guide caps 2000 are connected to insertion and extraction tool 3000, the longitudinal axis 2200 and the tool longitudinal axis 3400 may be coaxial, such that extraction tool 3000 is generally perpendicular to bone plate 1000 when extracting or inserting drill guide caps 2000. The extraction tool 3000 may also be used as a drill guide when connected to guide caps 2000, and extraction tool 3000 may generally remain perpendicular to bone plate 1000 and coaxial to grill guide cap 2000 when used as a drill guide. Extraction tool 3000 may be used to facilitate placing a drill bit connected to a drill (not shown) into extraction tool bore 3300 and through drill guide cap 2000, for drilling into bone, when bone plate 1000 is positioned against the bone.

Referring still to FIGS. 1-3, in a preferred method of assembly, guide caps 2000 are threadably pre-assembled on plate 1000 in holes 1300. The pre-assembled plate 1000 and guide caps 2000 and are preferably supplied in a sterile package. Pre-assembly of the guide caps 2000 into the holes 1300 of plate 1000 is performed so that a surgeon does not have to thread the drill guide caps 2000 into plate 1000 before the plate 1000 is positioned on the bone during a surgical procedure. The pre-assembly can be done by the operating room technician or at the factory prior to packaging and sterilization.

Referring still to FIGS. 1-3, guide caps 2000 preferably include a hard, e.g., metal bore 2100. Guide caps 2000 may be made entirely of metal or have an outer plastic body with an insert such as a thin walled, molded metal tube. Additionally, guide caps 2000 may also be made entirely of plastic. Insertion/extraction tool 3000 may be made from hard metal. The insertion/extraction tool 3000 may be connectable to guide cap 2000, such that extraction tool 3000 may line the inner circumference or perimeter of guide cap 2000 for the height of guide cap 2000. Thus, when extraction tool 3000 is received in one of guide caps 2000 and the drill bit is introduced into extraction tool bore 3300 of extraction tool 3000, any material from guide cap 2000 in contact with the drill bit is minimized or eliminated during drilling. This minimal contact allows guide cap 2000 to be made of plastic due to minimal risk of plastic debris being produced during drilling. The ability to manufacture the guide caps 2000 from plastic reduces manufacturing cost, and the use of the insertion/extraction tool 3000 mitigates any risk of plastic debris generation due to contact between guide caps 2000 made from plastic and the drill bit.

Referring again to FIG. 3, after the drill bit has prepared a hole, the extraction tool may be turned to unscrew cap 2000. Cap 2000 and extraction tool 3000 are adapted to be separable when a first axial force is applied to cap 2000 along longitudinal axis 2200 in a first direction and a second force is applied to tool 3000 along the longitudinal axis 2200 in a second direction, where the second direction is opposite the first direction. Thus, guide caps 2000 preferably are retained on extraction tool 3000 until pulled apart, after which, the extraction tool 3000 may be used for the next hole.

Figure 4:
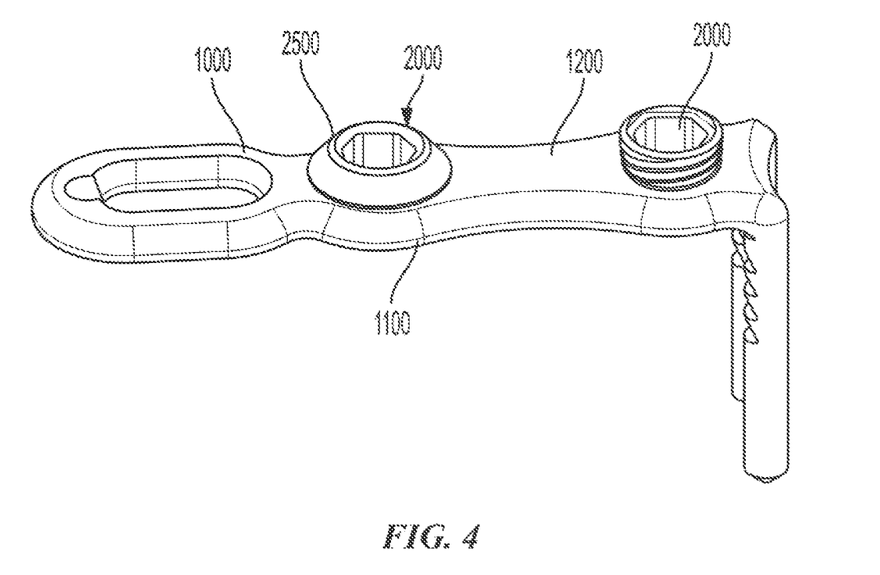
FIG. 4 shows a close-up perspective view of FIG. 1 including the bone plate with inserted guide caps.
Figure 5:
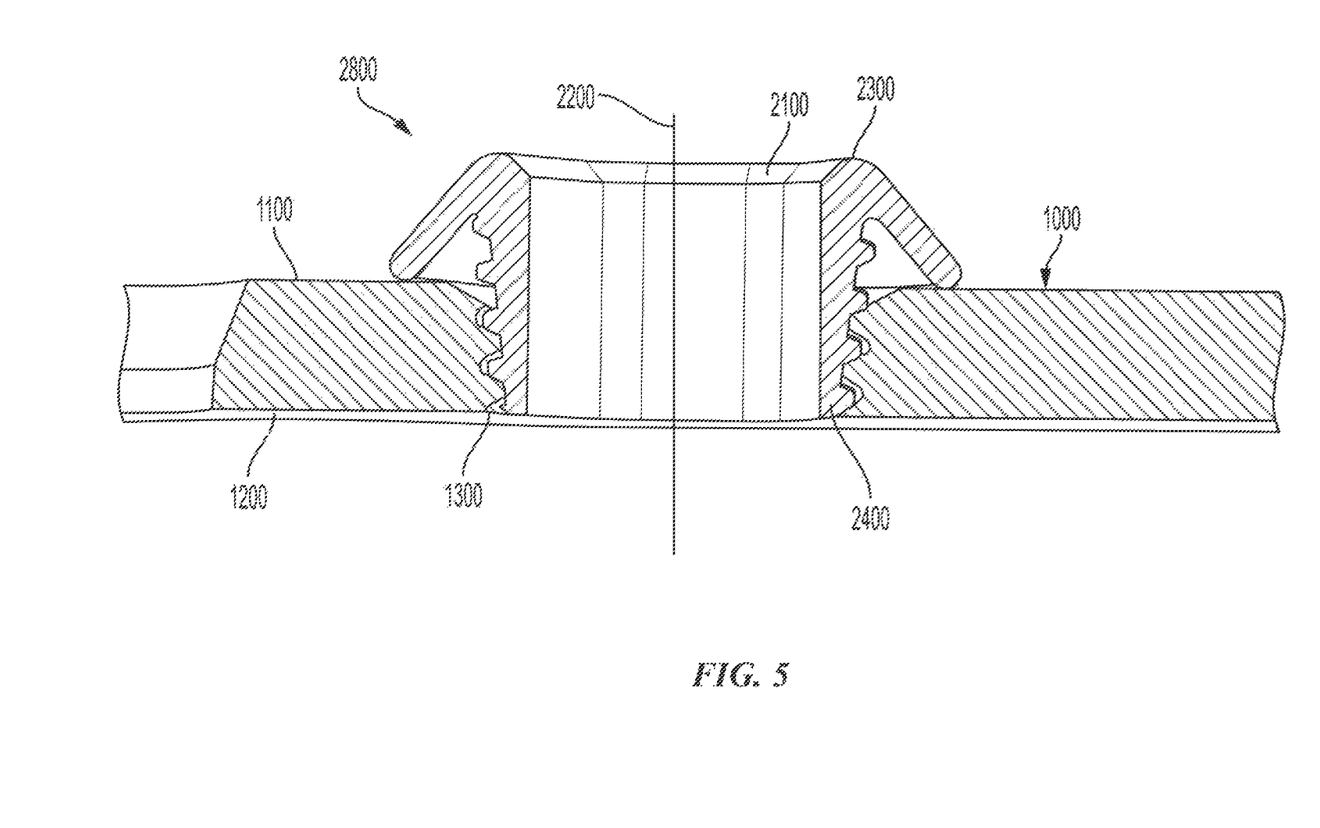
FIG. 5 shows a cross-sectional view of FIG. 1 including the bone plate with inserted guide caps.

Referring now to FIGS. 4-5, guide cap 2000 further has a flexible flange 2800 extending from and around proximal end 2300 of guide cap 2000. Flange 2800 extends from proximal end 2300 of guide cap 2000 toward distal end 2400 and forms an acute angle between the threaded exterior portion of guide cap 2000 and flange 2800.

The flange 2800 or "umbrella top" feature may be on the proximal portion 2300 of guide cap 2000. A combination of this umbrella top feature, the plate 1000, and cap 2000 has nearly no lip edge and thus may be easier for user to slide the assembled construct of guide cap 2000 and bone plate 1000 under soft tissue. The umbrella top is also flexible which allows it to flex and adapt to thicker or thinner plates 1000; thus, the same guide pin 2000 can be used for a variety of plate (e.g. plate 1000) thicknesses instead of having to fit a uniquely sized guide cap 2000 to each individual plate (e.g. plate 1000) thickness.

One advantage of the present invention, is the low profile of guide caps 2000 connected to plate 1000, compared to the prior art. The term "low profile" is understood to mean minimally extending from the bone surface. This makes the placement of plate 1000 much easier, compared to the prior art, because in some surgical procedures require a surgeon to slide a plate under an incision or under a tendon/ligament. Other pre-assembled plate and guide combinations are too tall thus requiring the surgeon to remove the assembled guides from the assembly and replace the guides once the plate is positioned on the anatomy, thereby defeating the purpose of a pre-assembled plate. The present system 10000 maintains a low profile until pre-assembled plate 1000 and guide caps 2000 are in place under whatever anatomy is required. In one embodiment, the guide caps may be equal to or less that the thickness of the bone plate. In other embodiments, the presence of a flexible flange 2800, may make the guide cap 2000 extend above the bone plate surface by approximately 1.5 mm or less. Thus, the guide caps 2000 either do not add to the thickness of the plate or in other embodiments, only minimally add to the thickness.

Another advantage is that extraction tool 3000 for guide caps 2000 is built into the drill guide cap 2000 and removal tool 3000 combination. This may help to minimize wait and preparation times between the surgical steps. For example, in the prior art, drill guide caps or pins are removed using a surgical screw driver, commonly the one used to insert surgical screws. In an embodiment of this invention, the extraction tool 3000 may be an extension of the guide caps 2000, for drilling and guide cap removal. While the extraction tool 3000 may be used to remove guide caps 2000, the surgical screw driver may be prepared for inserting screws, thus minimizing wait and preparation times. Other systems in the prior art require guide caps to be removed with the surgical screw driver that is also used to insert the screw which means the two processes must be done in series thus requiring more time.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A bone plate system for fixation of a fractured bone, the system comprising:
   a bone plate comprising:
      an elongate plate body extending from a proximal end to a distal end and including a bone contacting first surface and an opposite generally planar second surface;
      a first fastener aperture extending through the first and second surfaces of the plate body;
      a second fastener aperture extending through the first and second surfaces of the plate body;
      a first leg member formed integral with the distal end of the plate body and extending away from the first surface of the plate body, the first leg member including fixation projections configured for engagement with bone; and
      a second leg member formed integral with the distal end of the plate body and extending away from the first surface of the plate body, the second leg member including fixation projections configured for engagement with bone; and
   a plurality of fasteners, each fastener configured for insertion within at least one of the first fastener aperture or the second fastener aperture;
   wherein the plate body extends along a longitudinal plate body axis from the proximal end to the distal end of the plate body, the plate body further including a first side extending between the first and second surfaces of the plate body and an opposite second side extending between the first and second surfaces of the plate body;
   wherein the first and second fastener apertures are aligned along the longitudinal plate body axis;
   wherein the first and second leg members extend away from the longitudinal plate body axis the first and second leg members extending from the bone contacting first surface;

wherein the plate body defines a first plate width at a location between the first and second fastener apertures and larger second and third plate widths at locations corresponding to the first and second fastener apertures, respectively; and wherein a plate width is defined at the distal end of the plate body where the first and second leg members extend away from the first surface of the plate body, the plate body gradually increasing in width from the third plate width at the second fastener aperture to the plate width at the distal end of the plate body.

2. The bone plate system of claim 1, wherein the fixation projections comprise serrations.

3. The bone plate system of claim 1, wherein the fixation projections comprise teeth.

4. The bone plate system of claim 1, wherein each of the plurality of fasteners comprises a head portion and a shaft portion, the shaft portion defining a shaft length.

5. The bone plate system of claim 4, wherein the shaft length of at least one of the plurality of fasteners is different from the shaft length of at least one of the other plurality of fasteners.

6. A bone plate for fixation of a fractured bone, comprising:
- an elongate plate body extending along a longitudinal plate body axis from a proximal end to a distal end, the plate body including a bone contacting first surface and an opposite second surface, the plate body defining a generally flat shape along the longitudinal plate body axis from the proximal end to the distal end;
- a first fastener aperture extending through the first and second surfaces of the plate body;
- a second fastener aperture extending through the first and second surfaces of the plate body;
- a first leg member extending from the distal end of the plate body and formed integral therewith; and
- a second leg member extending from the distal end of the plate body and formed integral therewith;

wherein the first and second leg members extend away from the longitudinal plate body axis the first and second leg members extending from the bone contacting first surface;

wherein the plate body further includes a first side extending between the first and second surfaces of the plate body and an opposite second side extending between the first and second surfaces of the plate body;

wherein the first and second fastener apertures are aligned along the longitudinal plate body axis;

wherein the plate body defines a first plate width at a location between the first and second fastener apertures and larger second and third plate widths at locations corresponding to the first and second fastener apertures, respectively; and wherein a plate width is defined at the distal end of the plate body, the first and second sides of the plate body diverging away from the longitudinal plate body axis from the third plate width at the second fastener aperture to the plate width at the distal end of the plate body.

7. The bone plate of claim 6, wherein the first and second leg members each include a plurality of fixation elements.

8. The bone plate of claim 6, wherein the first and second leg members are substantially cylindrical.

9. The bone plate of claim 6, wherein the first leg member extends from the distal end of the plate body at a location adjacent to the first side, and wherein the second leg member extends from the distal end of the plate body at a location adjacent to the second side.

* * * * *